United States Patent
Titone et al.

(10) Patent No.: US 7,941,583 B2
(45) Date of Patent: May 10, 2011

(54) CONTROLLED FREQUENCY CORE PROCESSOR AND METHOD FOR STARTING-UP SAID CORE PROCESSOR IN A PROGRAMMED MANNER

(75) Inventors: Jean-Michel Titone, Pessac (FR); Michel Coignard, Cestas Gazinet (FR)

(73) Assignee: Thales (FR)

( * ) Notice: Subject to any disclaimer, the term of this patent is extended or adjusted under 35 U.S.C. 154(b) by 0 days.

(21) Appl. No.: 12/374,664

(22) PCT Filed: Jul. 11, 2007

(86) PCT No.: PCT/EP2007/057129
§ 371 (c)(1),
(2), (4) Date: Jan. 21, 2009

(87) PCT Pub. No.: WO2008/009609
PCT Pub. Date: Jan. 24, 2008

(65) Prior Publication Data
US 2009/0327569 A1   Dec. 31, 2009

(30) Foreign Application Priority Data
Jul. 21, 2006  (FR) ..................... 06 06695

(51) Int. Cl.
*G06F 13/00* (2006.01)
*G06F 1/08* (2006.01)
*G06F 1/10* (2006.01)
(52) U.S. Cl. ................. 710/306; 713/1; 713/2; 713/501
(58) Field of Classification Search .................. 710/107, 710/306; 712/1, 2, 500, 501, 600; 713/1, 713/2, 500, 501, 600
See application file for complete search history.

(56) References Cited

U.S. PATENT DOCUMENTS

| | | | |
|---|---|---|---|
| 5,542,077 A | | 7/1996 | Johnson et al. |
| 5,935,255 A | * | 8/1999 | So et al. .................. 713/400 |
| 6,269,443 B1 | | 7/2001 | Poisner et al. |
| 6,845,444 B2 | * | 1/2005 | Su et al. .................. 713/1 |
| 6,928,540 B2 | * | 8/2005 | Chang .................. 713/1 |
| 2004/0255176 A1 | * | 12/2004 | George et al. .................. 713/320 |
| 2005/0268139 A1 | | 12/2005 | Chen |

FOREIGN PATENT DOCUMENTS
FR   2868563   10/2005

* cited by examiner

*Primary Examiner* — Glenn A Auve
(74) *Attorney, Agent, or Firm* — Stroock & Stroock & Lavan LLP

(57) ABSTRACT

Embodiments of the invention relate to a driven-frequency processor core. It comprises at least one processor, a non-volatile memory comprising a startup program, a bridge interconnecting buses linking the various components of said processor core, an interface component. The non-volatile memory comprises at least two frequency-related configurations each corresponding to an operating mode of the buses and/or of the components of said processor core. The non-volatile memory comprises an item of information which makes it possible to determine which operating mode should be used, said item of information being read by the interface component so as to determine the chosen mode. The interface component generates one or more clock signals, the frequency of said generated clock signals corresponding substantially to that described by the configuration of the chosen mode. The clock signals drive the buses and/or the components of said processor core. Embodiments of the invention also relate to a method for starting-up said processor core in a programmed mode. In particular, the invention is applied to processor cores embedded in aircraft.

10 Claims, 2 Drawing Sheets

Figure 1:
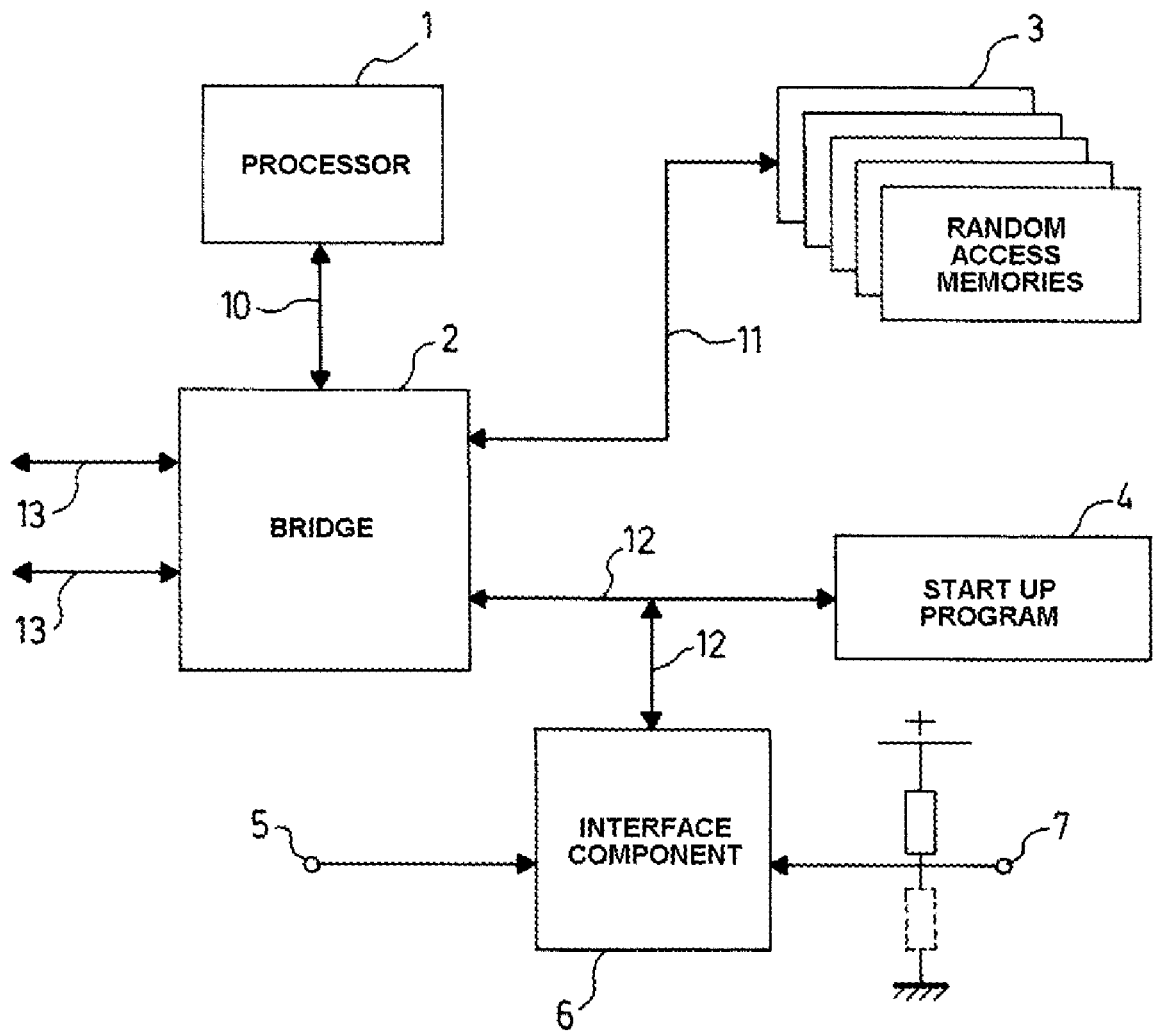

CONTROLLED FREQUENCY CORE PROCESSOR AND METHOD FOR STARTING-UP SAID CORE PROCESSOR IN A PROGRAMMED MANNER

CROSS-REFERENCE TO RELATED APPLICATIONS

This is a U.S. National Phase application under 35. U.S.C. §371 of International Application No. PCT/EP2007/057129, filed Jul. 11, 2007, and claims benefit of French Patent Application No. 06/06695, filed Jul. 21, 2006, both of which are incorporated herein in their entireties. The International Application was published in French on Jan. 24, 2008 as WO/2008/009609 under PCT 21 (2).

TECHNICAL FIELD

The invention relates to a driven-frequency processor core as well as to a method for starting up said processor core in a programmed mode. In particular, the invention applies to processor cores embedded in aircraft.

BACKGROUND OF THE INVENTION

A processor core, also known by the name CPU board, is an embedded electronic board comprising a processor carrying out calculations and processing operations. By way of example, a processor core can notably be embedded in a system of aircraft type where it performs a set of specific numerical calculations. A processor core, particularly in the aeronautical sector, carries out tasks of great criticality, such as for example managing the flight parameters, and must consequently exhibit significant reliability. To meet these constraints, a processor core is defined by a detailed and validated specification, and must form the subject of a validation/certification phase both from the conceptual and the hardware standpoint. It therefore follows notably that each modification of a characteristic of said processor core must form the subject of an upgrade of the specification followed by a study of risk and/or impact with regard to its reliability and those of the related equipment. It should of course be noted that such studies have a significant impact on the cost of the processor core.

In this context, one of the characteristics of a processor core liable to modification not only in the design phase but also in the course of the life cycle of said core is the frequency of the components included in the processor core. Modification of the frequency of the components included in the processor core is generally designated by the term "Throttling/Unthrottling" of a processor core. Furthermore, in relation to the above stated constraints, it is desirable that the "Throttling/Unthrottling" of the processor core be able to be performed without hardware modification ("without Hardware retrofit").

In order to carry out "Throttling/Unthrottling" of a processor core, it is known to include in the latter frequency multiplier components (PLL), and/or clock pilots comprising pull-up/pull-down clock drivers. Unfortunately, a hardware update ("retrofit") is inevitable to carry out the change of frequency of the processor core. This results notably in the impossibility of a dynamic change (that is to say while operating) of configuration, as well as the drawbacks set forth above.

In the computing sector, in particular that of personal computers, the basic input/output systems (BIOS) can in certain cases be provided with a device integrated into the motherboard making it possible to change the processor frequency and the bus frequency. However this solution does not exhibit characteristics of sufficient security and reliability for an embedded processor core. Specifically, if an erroneous value is written via the BIOS before the computer is restarted, the latter will be incapable of starting up again and will be in an unstable and unpredictable state.

SUMMARY OF THE INVENTION

The aim of the invention is notably to alleviate the aforesaid drawbacks. For this purpose, the subject of the invention is a processor core comprising at least one processor, a non-volatile memory comprising a startup program, a bridge interconnecting buses linking the various components of said processor core. The processor core includes an interface component, a non-volatile memory comprising at least two frequency-related configurations each corresponding to an operating mode of the buses and/or of the components of said processor core. The non-volatile memory includes an item of information making it possible to determine which operating mode should be used. Said item of information is read by the interface component so as to determine the chosen mode. The interface component generates one or more clock signals. The frequency of said generated clock signals corresponds substantially to that described by the configuration of the chosen mode. The clock signals drive the buses and/or the components of said processor core.

Advantageously, when the reading by the interface component of the item of information about the chosen mode turns out to be impossible or erroneous, the interface component is adapted for choosing a default mode.

In an embodiment, the processor core includes a clock delivering a reference clock signal. The frequency of said reference clock signal is then multiplied by the interface component so as to generate the signals whose frequency corresponds substantially to that described by the configuration of the chosen mode.

The processor core can receive a protection signal, said signal allowing or disallowing, depending on its value, the writing of the item of information making it possible to determine which operating mode should be used. The item of information making it possible to determine which operating mode should be used is for example modifiable by programming of the non-volatile memory and/or by the processor.

The subject of the invention is also a method for starting up a processor core comprising at least one non-volatile memory comprising a startup program, a bridge interconnecting buses linking the various components of said processor core, an interface component, the non-volatile memory comprising at least two frequency-related configurations each corresponding to an operating mode of the buses and/or components of said processor core. The non-volatile memory includes an item of information making it possible to determine which operating mode should be used, said item of information being read by the interface component so as to determine the chosen mode. The method includes the following steps:

- a step of powering-up the processor core, the components of the processor core being maintained by the interface component in a disabled state;
- a step where the interface component prohibits the resetting to zero of the non-volatile memory;
- a step of read-access by the interface component to the information relating to the selected operating mode and the associated configuration contained in the non-volatile memory;

a step of generation by the interface component of one or more signals whose frequency corresponds to the configuration of the selected mode, said signals driving the buses and/or the components of said processor core;

a step of re-enabling by the interface component of the various components.

Advantageously, after the step of powering-up the processor core, the method includes a step of timing out until the reference clock signal meets certain defined stability criteria.

Advantageously, if the reading by the interface component of the item of information about the mode chosen in the read-access step turns out to be impossible or erroneous, the interface component chooses in the step, instead of the inaccessible or erroneous item of information, a default mode.

In an embodiment, after the step of generation by the interface component of one or more signals whose frequency corresponds to the configuration of the selected mode, the method includes a timeout step until the buses attain their target frequency in a stable manner.

In another embodiment, in the step of generating signals by the interface component, the latter determines multiplicative factors to be applied to the frequency of a reference clock signal so as to obtain one or more signals whose frequency corresponds to that described in the configuration corresponding to the selected mode.

The invention has notably the advantages that it makes it possible to make secure and to enhance the reliability of managing changes of bus frequencies. It can be totally managed at the hardware level of the processor core. Embodiments of the invention permit hardware control of the restart configuration with an ever valid default configuration, even in the event of erasure of the configuration storage area.

Figure 2:
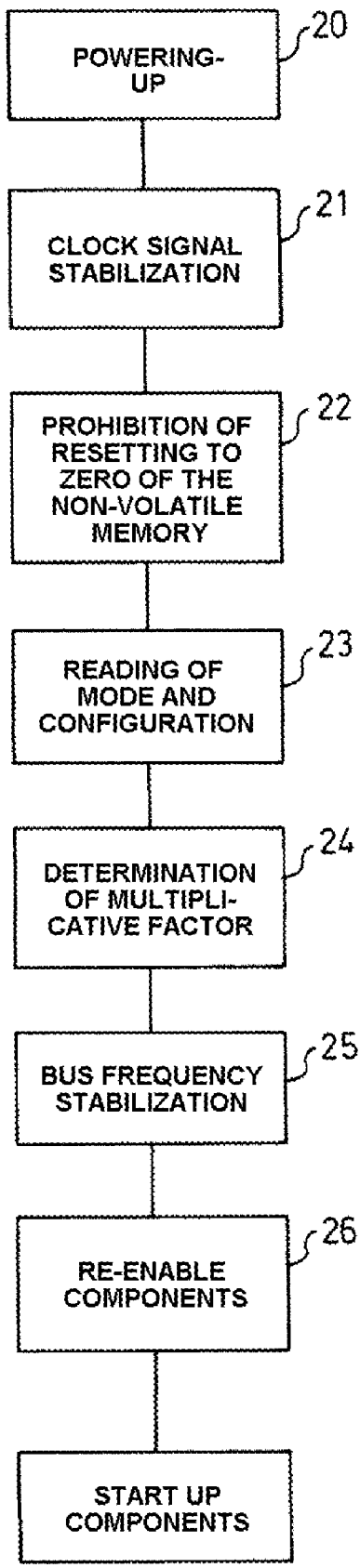

Other characteristics and advantages of embodiments of the invention will become apparent with the aid of the description which follows, given with regard to the appended drawings which represent:

FIG. 1, a schematic of the processor core according to embodiments of the invention;

FIG. 2, a diagram of a method for starting up the processor core in a programmed mode according to embodiments of the invention;

FIG. 1 shows as a schematic a processor core according to embodiments of the invention. The driven-frequency processor core according to embodiments of the invention include notably at least one processor 1. The processor 1 is adapted notably for performing numerical calculations. The processor 1 communicates via at least one processor bus 10 to the other components of the processor core. The processor core can further comprise some random access memory 3, for example memory of DDR-SDRAM type. The random access memory 3 is accessible by way of a memory bus 11. The processor core can also comprise external buses 13, such as for example one or more PCI buses. The processor core includes a non-volatile memory 4 comprising the startup program. The non-volatile memory 4 can for example be a bank of FLASH memories. The processor core includes an interface component 6 between a clock 5 (for example, a quartz), a multiplex peripheral bus 11 to which is connected notably the non-volatile memory 4 comprising the startup program, and optionally a protection signal 7 for the startup program. The interface component 6 can be a programmable component. The processor core includes a bridge 2 charged with managing and interconnecting the buses of said core.

The startup program included in the non-volatile memory 4 includes the instructions necessary for starting up the processor core. The non-volatile memory 4 includes at least two frequency-related configurations, each corresponding to an operating mode of the buses and/or of the components of the processor core: a throttled mode, an unthrottled mode. The operating frequency of the buses in unthrottled mode is greater than, or indeed equal to, the throttled mode. The non-volatile memory 4 includes an item of information, contained for example in memory locations, making it possible to determine which operating mode should be used for the next startup of the processor core. The configuration relating to a given operating mode describes notably the frequency at which the buses should operate and optionally, if this turns out to be relevant, the components of the processor core. The protection signal 7 allows or disallows, depending on its value, the writing of the item of information making it possible to determine which operating mode should be used. For example, when the protection signal 7 is received, it is possible to read but not to write the item of information making it possible to determine which operating mode should be used. Conversely, when the protection signal 7 is not received, it is possible to write said item of information. The item of information making it possible to determine which operating mode should be used is modifiable by programming of the non-volatile memory 4 and/or by the processor 1.

The interface component 6 receives a reference clock signal 5 originating from the clock. The interface component 6 reads the item of information about the chosen mode, included in the non-volatile memory 4. If the reading of the item of information about the chosen mode turns out to be impossible or erroneous (it being possible for detection to be for example ensured by an error checking mechanism of cyclic redundancy check type or else by verifying that the values read belong to a span of predefined value), the interface component 6 chooses a default mode, corresponding for example to the lowest frequency of the various buses and/or components of the processor core. The default mode can notably be programmed in the very heart of the interface component 6. This mechanism ensures an additional security level, avoiding notably the use of a value which is written in error or is wrong in the non-volatile memory 4. Depending on the mode selected and on the associated configuration included in the non-volatile memory 4, the interface component 6 generates one or more clock signals on the basis of the reference clock signal 5. These generated clock signals have a frequency corresponding substantially to that described in the configuration of the selected mode. These generated clock signals serve to drive the buses and/or the components of the processor core. These clock signals will then be used for each bus and/or component and will then determine their operating frequency. Thus, if the configuration describing the throttled mode corresponds to an operating frequency of 100 MHz for the processor bus 10, the memory bus 11, the interface component will generate a signal of frequency substantially equal to 100 MHz, thus forcing the processor 1, the processor bus 10, the random access memory 3 and the memory bus 11 to operate at 100 MHz. Thus, if the configuration describing the unthrottled mode corresponds to an operating frequency of 133 MHz for the processor bus 10, the memory bus 11, the interface component will generate a signal of frequency substantially equal to 133 MHz, thus forcing the processor 1, the processor bus 10, the random access memory 3 and the memory bus 11 to operate at 133 MHz. It is of course possible, if the processor core can moreover support it, to define different bus frequencies for one and the same given mode according to the components, and operate the memory bus 11 at a different speed from the processor bus 1.

FIG. 2 illustrates by a diagram a method for starting up the processor core in a programmed mode according to embodiments of the invention. The elements identical to the elements already presented in the other figures bear the same references. The startup method according embodiments of to the invention describe the sequence for starting up a processor core according to embodiments of the invention (for example, that illustrated in FIG. 1) in a given operating mode. In a step 20, the processor core is powered up. The components of the processor core (such as the processor 1, the bridge 2, etc.) are maintained in a disabled state (also known as "reset"). A step 21 marks time until the clock signal emitted by the clock 5 meets certain defined stability criteria. The interface component 6 prohibits in a step 22 the resetting to zero of the non-volatile memory 4 comprising the startup program. Then in a step 23, the interface component 6 read-accesses the information contained in the non-volatile memory 4, in particular the selected operating mode and the associated configuration. If the reading by the interface component 6 of the item of information about the chosen mode turns out to be impossible or erroneous, the interface component 6 chooses in step 23 instead of the inaccessible or erroneous item of information a default mode, corresponding for example to the lowest frequency of the various buses and/or components of the processor core. On the basis of this information, in a step 24, the interface component 6 generates one or more signals whose frequency corresponds to the configuration of the selected mode, said signals driving the buses and/or the components of said processor core. For this purpose, the interface component determines the multiplicative factor to be applied to the frequency of the clock signal 5 so as to obtain a signal whose frequency corresponds to the configuration corresponding to the selected mode. Thus, this multiplicative factor depends on the configuration of the selected mode and is therefore different depending on whether the active mode selected is the throttled mode or the unthrottled mode. On the basis of this multiplicative factor, the interface component 6 generates a signal whose frequency corresponds to the configuration of the selected mode. This signal is thereafter used by the various buses of the processor core. In a timeout step 25, a timeout makes it possible to wait for the buses to attain their target frequency in a stable manner. Then, the interface component 6 re-enables the various components (processor 1, bridge 2, etc.), in a step 26. The processor 1, the bridge 2, the buses, and the other components can then start up in a step 27 in the selected mode, throttled or unthrottled. The processor core is then usable by the operating system in the chosen operating mode.

The operating mode can be changed to another mode. To perform this change, it is possible for example to remove the protection of the non-volatile memory comprising the startup program by modifying at input the protection signal 7 so as to allow writing. The chosen mode can then be rewritten either by programming (for example using a cable of JTAG type) or via the processor 1. The new configuration will be taken into account only after a shutdown/power-up.

The invention claimed is:

1. A processor core comprising:
   at least one processor;
   a plurality of buses linking components of the processor core;
   a bridge interconnecting the plurality of buses;
   an interface component;
   a non-volatile memory comprising:
   a memory containing instructions for a startup program;
   the startup program including at least two frequency-related configurations, wherein each configuration corresponds to an operating mode of the buses and/or components of said processor core; and
   an item of information making it possible to determine which operating mode should be used, said item of information being read by the interface component so as to determine a chosen operating mode,
   wherein the interface component generates one or more clock signals, a frequency of said generated clock signals corresponding substantially to a frequency described by the configuration of the chosen operating mode, said clock signals driving the plurality of buses and/or the components of said processor core.

2. The processor core as claimed in claim 1, wherein if reading the item of information about the chosen operating mode by the interface component is impossible or erroneous, the interface component is adapted to choose a default mode.

3. The processor core as claimed in claim 2, comprising: a clock to deliver a reference clock signal, wherein a frequency of said reference clock signal is multiplied by the interface component so as to generate signals whose frequency corresponds substantially to the frequency described by the configuration of the chosen operating mode.

4. The processor core as claimed in claim 3, wherein the processor core receives a protection signal, a value of the protection signal allowing or disallowing writing to the non-volatile memory of the item of information making it possible to determine which operating mode should be used.

5. The processor core as claimed in claim 4, wherein the item of information making it possible to determine which operating mode should be used is modifiable by programming of the non-volatile memory and/or by the processor.

6. A method for starting up a processor core, the processor core comprising:
   at least one processor;
   a plurality of buses linking components of the processor core;
   a bridge interconnecting the plurality of buses;
   an interface component; and
   a non-volatile memory comprising:
   a memory containing instructions for a startup program;
   the startup program including at least two frequency-related configurations, wherein each configuration corresponds to an operating mode of the buses and/or components of said processor core; and
   an item of information making it possible to determine which operating mode should be used and an associated configuration, said item of information being read by the interface component so as to determine a chosen operating mode,
   the method comprising the following steps:
   powering-up the processor core, the components of the processor core maintained in a disabled state by the interface component;
   prohibiting the resetting to zero of the non-volatile memory by the interface component;
   permitting read-access by the interface component to the information to determine which operating mode should be used and the associated configuration contained in the non-volatile memory;
   generating by the interface component one or more signals whose frequency corresponds to the configuration of the chosen mode, said signals used to drive the buses and/or the components of said processor core; and
   re-enabling of the components of the processor core by the interface component.

7. The method as claimed in claim 6 characterized in that after the step of powering-up the processor core, the method further comprises a step of timing out until a reference clock signal meets certain defined stability criteria.

8. The method as claimed in claim 7 wherein, after the step of permitting read-access by the interface component, if reading by the interface component of the item of information about the mode chosen in the read-access step is impossible or erroneous, the interface component chooses a default mode.

9. The method as claimed in claim 8 wherein after the step of generating by the interface component of one or more signals whose frequency corresponds to the configuration of the chosen mode, the method comprises the step of timing-out until the buses attain their target frequency in a stable manner.

10. The method as claimed in claim 9, wherein the step of generating signals by the interface component further comprises the step of determining by the interface component of multiplicative factors to be applied to the frequency of the reference clock signal so as to obtain one or more signals whose frequency corresponds to the frequency described in the configuration corresponding to the chosen mode.

\* \* \* \* \*